(12) United States Patent
Herrlein et al.

(10) Patent No.: US 6,446,495 B1
(45) Date of Patent: Sep. 10, 2002

(54) METHOD FOR ASSESSING DISPOSABLE ABSORBENT ARTICLES

(75) Inventors: Mathias Kurt Herrlein, Frankfurt a.M. (DE); Muir Charles Robertson, Cincinnati, OH (US); Alexander Berk, Frankfurt a.M. (DE); Ulrich Kleinsteuber, Bever (BE); Manfred Plischke, Steinbach/Ts (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/446,208

(22) PCT Filed: Jun. 22, 1998

(86) PCT No.: PCT/IB98/00953
§ 371 (c)(1),
(2), (4) Date: Mar. 2, 2000

(87) PCT Pub. No.: WO98/58606
PCT Pub. Date: Dec. 30, 1998

(30) Foreign Application Priority Data

Jun. 25, 1997 (EP) ............................................. 97110328

(51) Int. Cl.[7] .............................................. G01N 25/26
(52) U.S. Cl. ............................................. 73/73; 73/866
(58) Field of Search .................................... 73/73, 866

(56) References Cited

U.S. PATENT DOCUMENTS

| | | | |
|---|---|---|---|
| 3,952,584 A | * 4/1976 | Lichstein | .......................... 73/73 |
| 4,631,062 A | * 12/1986 | Lassen et al. | ................ 604/378 |
| 5,356,403 A | * 10/1994 | Faulks et al. | ................ 604/378 |
| 5,382,246 A | * 1/1995 | Kawano | .................. 604/385.2 |

FOREIGN PATENT DOCUMENTS

| | | | |
|---|---|---|---|
| EP | 0 358 031 A2 | 3/1990 | ............ A61F/13/15 |
| EP | 0 719 531 A1 | 7/1996 | ............ A61F/13/15 |
| GB | 2 197 206 A | 5/1988 | ............ A61F/13/16 |

\* cited by examiner

Primary Examiner—Hezron Williams
Assistant Examiner—Nashmiya Fayyaz
(74) Attorney, Agent, or Firm—Michael S. Kolodesh; Jay A. Krebs; Ken K. Patel

(57) ABSTRACT

The present invention provides a new method for assessing disposable absorbent articles with regard to their impact on skin aeration by measuring relative humidity values in a mannequin test set up.

7 Claims, 3 Drawing Sheets

METHOD FOR ASSESSING DISPOSABLE ABSORBENT ARTICLES

FIELD OF INVENTION

The present invention relates to a method allowing to better assess disposable absorbent articles such as diapers, incontinence articles, sanitary towels, training pants and the like in view of their impact on the hydration status of the skin of the wearer.

BACKGROUND OF THE INVENTION

Disposable, absorbent articles such as diapers, incontinence articles, sanitary towels, training pants and the like are well known in the art. Typically, disposable absorbent articles comprise a liquid previous topsheet that faces the wearer's body, a liquid impervious backsheet that faces the wearer's clothing, an absorbent core interposed between the liquid previous topsheet and the backsheet, and means to keep the core in fixed relation to the wearer's body.

Also well known in the art are methods to assess the performance of such articles, such as acquisition tests, capillary rewet tests or collagen rewet tests. All current methods assess either the liquid handling capability of an absorbent article or the impact of liquid more or less well retained by an article on human skin or materials representing human skin.

Thus, all methods fail to provide meaningful results where either no direct contact is present between the skin of the wearer, i.e. where the gas or vapour phase dominates the physical conditions.

Henceforth, it is an object of the present invention to provide an easy to use tool for assessing the performance of absorbent articles not only with regard to liquid handling performance, but also with regard to the vapour phase inside the article.

SUMMARY

The present invention provides a new method for assessing disposable absorbent articles with regard to their impact on skin aeration by measuring relative humidity values in a mannequin test set up.

DETAILED DESCRIPTION

Figure 1:
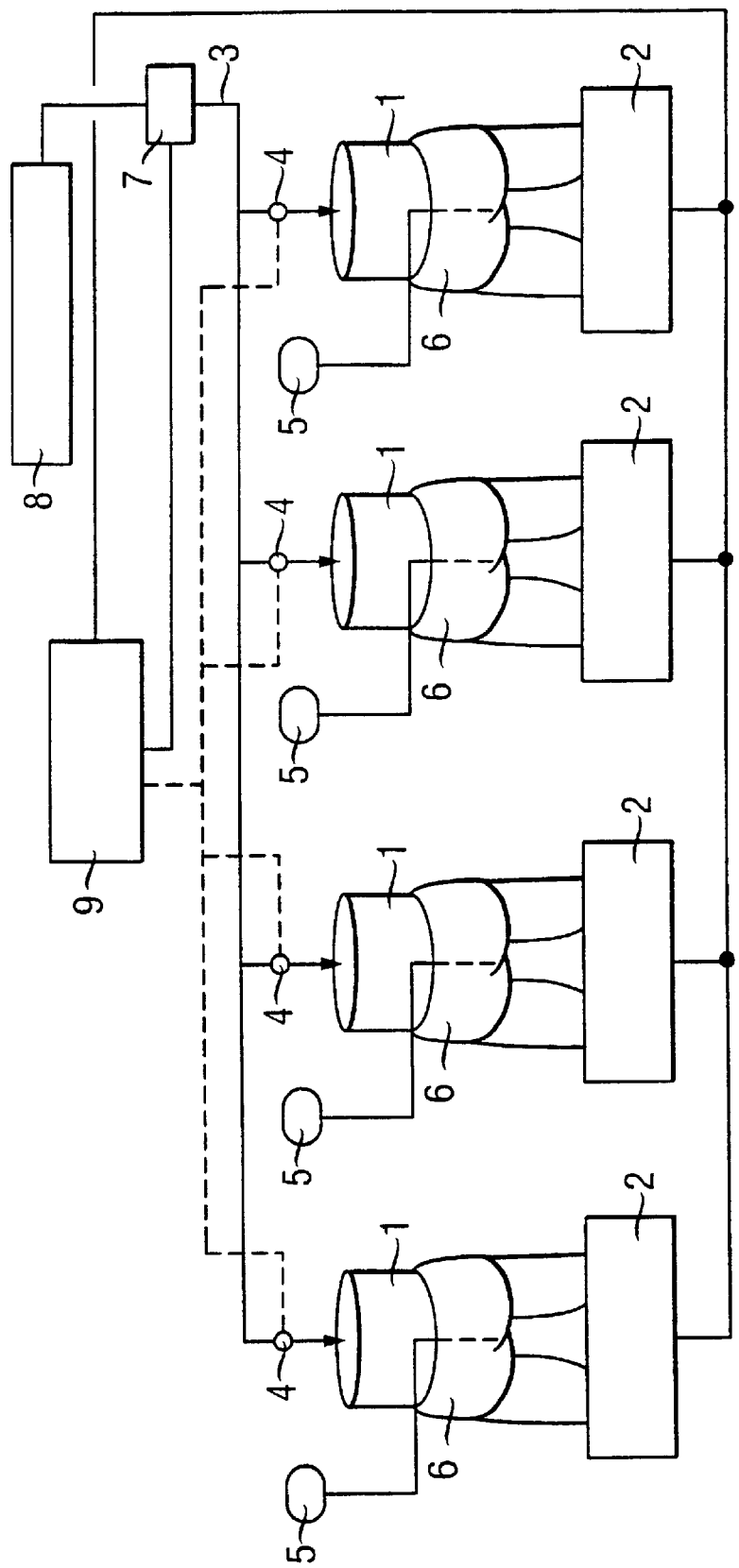
FIG. 1 is showing the test equipment set up for the Mannequin Relative Humidity testing

The present invention relates to a method, which can be executed in a laboratory so as to allow assessment and comparison of various absorbent articles.

As used herein, the term "absorbent articles" refers to devices which absorb and contain body exudates, and, more specifically, refers to devices which are placed against or in proximity to the body of the wearer to absorb and contain the various exudates discharged from the body, primarily urine.

The term "disposable" is used herein to describe absorbent articles which are not intended to be laundered or otherwise restored or reused as an absorbent article (i.e., they are intended to be discarded after use and, preferably, to be recycled, composted or otherwise disposed of in an environmentally compatible manner).

a) an absorbent core (which may consist of sub-structures and/or wrap materials), including on the side oriented towards the wearer a topsheet, which forms the inner surface and which—at least in certain regions thereof—allows the exudates to penetrate through, and including on the opposite side a backsheet which forms the outer surface of the article and which separates the absorbent core from the outside, such as the clothing of the wearer.

b) chassis elements comprising features like closure elements or elastication to maintain the article on the wearer. Also comprising a topsheet which forms the inner surface an a backsheet. The backsheet and the topsheet materials of the absorbent core can be unitary with respective materials in the chassis regions, i.e. the backsheet can cover the absorbent core and the same material or sheet may extend into the chassis region, thereby, for example, covering features like the leg elastics or the like.

Such articles can be baby diapers, either of the "taped diaper" type comprising closure means so as to apply an article which may be produced in an essentially flat configuration around the body of the wearer, or of the "pant style" diaper with closed side seams, or adult incontinence article, and the like.

In order to be able to compare absorbent articles for varying end use conditions, or differently sized articles, the "design capacity" has been found to be a suitable measure.

For example, babies are representing a typical usage group, but even within this group the amount of urine loading, frequency of loading, composition of the urine will vary widely from smaller babies (new-born babies) to toddlers on one side, but also for example among various individual toddlers.

Another user group may be larger children, still suffering from a certain form of incontinence.

Also, incontinent adults can use such articles, again with a wide range of loading conditions, generally referred to as light incontinence ranging up to severe incontinence.

Whilst the man skilled in the art will readily be able to transfer the teaching to other sizes for further discussion, focus will be put on the toddler sized babies. For such user, urine loadings of up to 75 ml per voiding, with on an average of four voidings per wearing period resulting in a total loading of 300 ml.

Henceforth, such articles being able to cope with such requirements should have the capability of picking up such amounts of urine, which will be referred to for the further discussion as "design capacity".

These amounts of fluids have to be absorbed by materials which can ultimately store the bodily fluids, or at least the aqueous parts of these, such that—if any—only little fluid is left on the surface of the article towards the wearer's skin. The term "ultimate" refers in one respect to the situation as in the absorbent article at long wearing times, in the other respect to absorbent materials which reach their "ultimate" capacity when being equilibrated with their environment. This can be in such an absorbent article under real in-use conditions after long wearing times, or this also can be in a test procedure for pure materials or material composites. As many of the. processes under consideration have asymptotic kinetic behaviour, one skilled in the art will readily consider "ultimate" capacities to be reached when the actual capacity has reached a value sufficiently close to the asymptotic endpoint, e.g. relative to the equipment measurement accuracy.

As an absorbent article can comprise materials which are primarily designed to ultimately store fluids, and other materials which are primarily designed to fulfill other functions such as acquisition and/or distribution of the fluid, but may still have a certain ultimate storage capability, suitable core materials according to the present invention are described without attempting to artificially separate such functions. Nonetheless, the ultimate storage capacity can be determined for the total absorbent core, for regions thereof, for absorbent structures, or even sub-structures, but also for materials as being used in any of the previous.

In case of applying the present invention to other articles requiring different end-uses, one skilled in the art will be able to readily adopt the appropriate design capacities for other intended user groups.

In order to determine or evaluate the Ultimate Design Storage Capacity of an absorbent article, a number of methods have been proposed.

In the context of the present invention, it is assumed, that the Ultimate Storage Capacity of an article is the sum of the ultimate absorbent capacities of the individual elements or material. For these individual components, various well established techniques can be applied as long as these are applied consistently throughout the comparison. For example, the Tea Bag Centrifuge Capacity as developed and well established for superabsorbent polymers can be used for such SAP materials, but also for others (see above).

Once the capacities for the individual materials are known, the total article capacity can be calculated by multiplying these values (in ml/g) with the weight of the material used in the article.

For materials having a dedicated functionality other than ultimate storage of fluids—such as acquisition layers and the like—the Ultimate Storage Capacity can be neglected, either as such materials do in fact have only very low capacity values compared to the dedicated ultimate fluid storage materials, or as such materials are intended to not be loaded with fluid, and thus should release their fluid to the other ultimate storage materials.

With such definitions, so-called "panty liners" exhibit very low Ultimate Storage Capacities of a few ml or less. Catamenial pads have often up to about 20 ml, light urinary incontinence articles have for example 75 ml or about 90 ml, medium urinary incontinence articles, or also smaller baby diaper can have about 165 ml, and toddler size baby diapers reaching 300 ml or more, and severe adult incontinence article having 600 ml or more of Ultimate Storage Capacity.

The present invention will be particularly useful for articles which—in addition to good liquid handling capability—also allow good aeration of the skin of the wearer, such as by the use of materials which are permeable to gases such as air or water vapour.

Examples for such materials are so called microporous films, for example as can be provided by Mitsui Co. under the designation . . . Such films can be made by producing a polymer film such as made from Polythylene, further comprising filler particles, such as Calcium-Carbonate. After having formed a film wherein these filler particles are embedded into a matrix of polymeric material, the film can be mechanically treated so as to strain and stretch the polymeric materials permanently, thereby creating small cracks around the non-deforming filler particles. The cracks are sufficiently small to allow gas molecules of the gas phase to pass through, but prevent liquids from penetrating. Thus the transport mechanisms is slow flow in capillaries.

Of course, such materials must provide certain liquid barrier properties so as to prevent liquid penetrating through.

With products as described in the above, conventional tests enabled to guide the product designer as to how assess the liquid handling behaviour, i.e. the liquid retention in an absorbent structure, or the pick up of the liquid into an absorbent structure. Thus the man skilled in the art was left at uncertainty when the design of the article did not lead to 100% contact between the absorbent article or at least absorbent core and the skin of the wearer. Also, it was difficult to assess the impact which breathable materials could have on the skin condition of the wearer.

Thus, the present invention provides a tool to allow better assessment and henceforth better design of absorbent articles.

The method of the present invention is using a conventional testing tool, a mannequin, and is extending its use to evaluate hitherto unforeseen properties, namely the relative humidity in the vapour phase of the article.

The basis for the testing equipment is a "Courtray Capability Baby Mannequin Tester" with 4 Maxi/Maxi Plus size mannequins (Generation'ANT') purchased at Courtray Consulting, Douai, FRA. For the test as executed, the "Girl loading" point has been found suitable to also provide meaningful comparative results for unisex or even "boy" products.

With this size of mannequin, also Maxi/Maxi Plus or equivalent diaper sizes have to be used. The present invention, however, can be adopted to other size mannequins suitable for other article sizes.

The second essential element for the present invention is a hygrometer, such as Hygrometer TFH 100 (certified Din ISO 9001) from Ebro Electronics, lngolstadt, FRG, having a probe diameter of about 13 mm and a probe length of about 200 mm with a pen-mark at 135 mm away from the tip of the probe.

The test stand is schematically shown in FIG. 1. The mannequins 1, placed on scales 2 are loaded with test fluid through tubings 3, controlled via valves 4. The sensor probe of the relative humidity measurement device 5 is positioned inside the test diaper 6. The fluid is pumped via pump 7 from the reservoir 8. The timing, flow rates, mannequin weights are registered and controlled by the computerised control unit 9, such that the mannequins are loaded in a staggered manner.

The test fluid applied for this test is a Synthetic Urine composed of 9 g NaCl; 1.11 g $Na_2HPO_4$; 2.69 g $KH_2PO_4$ diluted in 1000 ml deionized water. It is kept constantly at a temperature of 37.5° C.

The test is run under tightly controlled atmospheric conditions of room temperature (22±2° C.) and relative humidity (50±2%)

The details of the testing protocol are a follows:

1. Preparations: In order to apply a test diaper, the mannequin is put up-side down such as on a lab bench. The testing diaper is unfolded, a longitudinally centered fold is formed to allow easier fitting into the crotch region of the mannequin. Upon application of the folded diaper such that it contacts the mannequin in the crotch region, the leg-elastics are folded upwards (i.e. towards the upper region if this were a human wearer) in between the legs by sliding down but not inwards. It is important, that upon application the front end of the diaper and the rear end of the diaper are at leveled arrangement.

The mannequin is laid flat on the table, on its back, and the appropriate positioning of the leg cuffs, or further barrier cuffs is ensured. The diaper is closed such that a finger can be inserted between test specimen at the front upper core edge without undue force.

The hygrometer is inserted in back of the diaper on the mannequin such that the pen-mark on the Hygrometer probe (13.5 cm from lower end) is at level with back of the waist diaper absorbent core edge. This should coincide with a position of about 5 cm backwardly away from the "crotch point", i.e. the narrowest distance between the legs of the mannequin.

The mannequin is positioned in the upright ("standing") position.

2. Test execution: The automated mannequin test station is set up to deliver 75 ml gushes every 60 minutes over 4 hours, at a flow rate of 150 ml/min. As the complete test stand has four mannequins for parallel testing, loading occurs in a staggered pattern of 5 min intervals between mannequins.

Whilst the Hygrometer probe remains in the diaper in the same position over the entire 4 hrs wearing period, relative humidity reading is noted every 10 minutes between gushes beginning 5 minutes after each gush.

EXAMPLES

In order to further exemplify the benefits of the current invention, samples of different baby diapers have been submitted various test protocols as outlined herein. For comparability reasons, all were of comparable size, namely of for babies of about 9 to 18 kg, often called MAXI (or MAXI PLUS size) or "SIZE 4".

Basis for a product according to the present invention is a commercially available product, PAMPERS Baby Dry Plus Maxi/MAXI PLUS size as marketed by Procter & Gamble in Europe.

In order to improve the rewet performance of such articles, the core has been modified by the following steps:

First, chemically treated stiffened cellulosic material (CS) supplied by Weyerhaeuser Co., US under the trade designation of "CMC" functioning as an acquisition/distribution layer has a basis weight of about 590 g/m2. Second, an additional acquisition layer is introduced between the topsheet and said chemically treated stiffened cellulose layer, namely a high-loft chemically bonded nonwoven as supplied by FIBERTECH, North America under the designation type 6852. It is a chemically bonded PET fibre web of a basis weight of 42 g/m2 and a width of 110 mm over the full length of the absorbent core.

Thirdly, the cellulose material usage in the storage core underneath the chemically treated stiffened cellulosic material is reduced to about 11.5 g per pad. Fourth, the amount of superabsorbent material in this storage core is increased to about 16 g per pad. Superabsorbent material was supplied by Stockhausen GmbH, Germany under the trade name FAVOR SXM, type T5318.

Further, the conventional PE-backsheet has been replaced by a non-woven material, namely a hydrophobic, 23 gsm carded PP web such as supplied by SANDLER GmbH, Schwarzbach, FRG, under the designation VP 39522.

As comparative examples, following products have been evaluated:

Comparative example 2 differs only to example 1 in that the backsheet is a microporous film such as commercially available from MITSUI Toatsu, Japan, under the designation ESPOIRE NO.

Comparative example 3 is a commercially available product as marketed by UniCharm Corp. in Japan under the trade designation Moonyman, size 4. This product has a microporous film covering both the core and the chassis regions.

These products have been submitted to the relative absorbency mannequin test as well as to the PACORM test, with following results:

TABLE 1

| Sample | 1 | 2 | 3 |
|---|---|---|---|
| PACORM (mg) | 72 | 72 | 150 |
| Backsheet MVTR (g/m2/24 h) | 6000 | 3750 | 3300 |
| relative humidity (%) 1st gush | 48 | 48 | 48 |
| +5 min | 52 | 62 | 69 |
| +25 min | 53 | 59 | 73 |
| +55 min | 53 | 58 | 74 |
| 2nd gush | | | |
| +5 min | 59 | 73 | 92 |
| +25 min | 60 | 76 | 94 |
| +55 min | 61 | 78 | 94 |
| 3rd gush | | | |
| +5 min | 81 | 89 | 93 |
| +25 min | 83 | 90 | 95 |
| +55 min | 83 | 90 | 93 |
| 4rd gush | | | |
| +5 min | 89 | 92 | 93 |
| +25 min | 89 | 93 | 93 |
| +55 min | 89 | 93 | 92 |

Further Test Methods

Moisture Vapour Transmission Rate

The Moisture Vapour Transmission Rate is measuring the amount of moisture adsorbed by Calcium-Chloride in a "cup" like container covered with the test specimen from controlled outside air conditions (40±3° C./75±3% relative humidity).

The sample holding a cup is a cylinder with an inner diameter of 30 mm and an inside height from bottom to top flange of 49 mm. A flange having a circular opening to match the opening of the cylinder can be fixed by screws, and a silicone rubber sealing ring, matching the inner diameter, fits between the top flange and the cylinder. The test specimen is to be positioned such that it covers the cylinder opening, and can be tightly fixed between the silicone rubber sealing and the upper flange of the cylinder.

The equipment as well as the test specimen should be well adjusted to the temperatures, and the constant temperature/humidity chamber preferably has a size to accommodate up to 30 samples.

The absorbent desiccant material is CaCl2, such as can be purchased from Wako Pure Chemical Industries Ltd., Richmond, Va., US under the product designation 030-00525. If kept in a sealed bottle, it can be used directly. It also can be sieved to remove lumps, or excessive amounts of fines, if existing. It also can be dried at 200° C. for about 4 hrs.

15.0±0.02 g of CaCl2 are weighed into the cup, and tapped lightly so as to level it out, such that the surface is about 1 cm from the top of the cup.

The samples, which are cut to about 3.2 cm by 6.25 cm, are placed flat and overlapping with the seal over the opening, and the seal and the top flange are affixed by the screws without over tightening. The total weight of the cup assembly is accurately recorded on a four decimal places scale, and the assembly is placed into the constant temperature/humidity chamber.

After 5 hrs (without opening of the chamber), the sample is removed and immediately covered tightly with non-vapour permeable plastic film such as Saran wrap as commonly used in the U.S. After about 30 mins to allow for temperature equilibration, the plastic film cover is removed and the accurate weight of the assembly is recorded.

The MVTR value is then calculated from the moisture increase during these 5 hours through the 3 cm circular opening and then converted to units of "g/24 h/m2".

For each test, three replicates should be run, the resulting values will be averaged, and the result rounded to the nearest 100 value.

Overall, this method is applicable to thin films, multi layer laminates and the like. Experience has shown, that typical standard deviations range between 50 and 250 g/24 hr/m2 for averaged values of up to about 5000 g/24 hr/m2.

Due to this range, materials being considered to be essentially vapour impermeable such as conventional PE films, are reported as having a MVTR of about 200 g/24 hr/m2.

If the units for an MVTR value are omitted for simplicity, a material "having a MVTR value of 1000" should accurately be a material "having a MVTR value of 1000 g/24 hr/m2" according to this method.

Air Permeability

The air permeability is determined by measuring the time in which a standard volume of air is drawn through the test specimen at a constant pressure and temperature. This test is particularly suited to materials having relatively high permeability to gases, such as nonwovens, apertured films and the like.

The test is operated in a temperature and humidity controlled environment, at 22±2° C. and 50±2% relative humidity. The test specimen has to be conditioned for at least 2 hrs.

The test equipment as manufactured by Hoppe & Schneider GmbH, Heidelberg, Germany, under the designation "Textiluhr nach Kretschmar", is essentially a bellows in a vertical arrangement, with its upper end being mounted in a fixed position, and the lower end being releasably hold at its upper position, which can be loosened by means of a release handle to slide under controlled conditions to the lower position, thereby increasing the volume inside the bellows by pulling air through the test specimen which is covering the air entering opening at the upper end of the bellows. The test specimen is firmly hold to cover the air entering opening by means of a fastening ring of 5 cm2 or 10 cm2 to allow for different samples sizes and/or different permeability ranges. If the 10 cm2 ring is used, the sample should be at least 55 mm wide, for the 5 cm2 ring at least 35 mm. For both, the samples should have a length of about 150 mm. Optionally, the sample holding device can comprise a stretching element, such as to enable measurement of elastic materials under stretched conditions.

The equipment comprises a stopwatch ($1/100$ sec) which automatically measures the time between the operation of the release handle thus starting the sliding of the bellows, and the bottom of the bellows reaching its lower end position.

The air permeability of the material can then be calculated by dividing a constant as supplied by the supplier for each equipment (for the present equipment K=200.000 for a tested area of 5 cm2, and 400.000 for an area of 10 cm2) by the time as measured in seconds, resulting in units of (I/cm2/sec.)

The test is repeated once for each test specimen, and should be repeated on 10 specimen to provide a representative basis for a material.

Liquid Impermeability
(Hydro-Head Test)

The test principle is to increase an adjustable water head of distilled water on the top side of a test specimen of about 64 cm2, such as a film or an other porous material.

A test specimen is cut to about 10 cm by 10 cm and placed over a sample plate, also of a size of 10 cm by 10 cm with a centred O-ring seal of about 8 cm diameter. The sample plate has a centred opening of about 7.6 cm diameter to allow observation of the bottom side of the test specimen during the test. The sample plate is carefully positioned under a 7.6 cm inner diameter perspex column of about 1 m height, with a mounting flange so as to conveniently allow tightening of the sample plate carrying the sample underneath by means of screws. Optionally, a mirror is positioned under the opening in the sample plate to ease the observation.

The cylinder has an sideways oriented opening of about 1 cm diameter to allow connection to a pump, about 1 cm above the sample when mounted. Optionally, a three-way-valve can be mounted in this connection to allow easier emptying of the column after the test.

The pump is set to raise the liquid head in the cylinder within 60±2 seconds to 25.4 cm.

Upon starting of the pump the bottom surface of the test specimen is watched. Upon the first drop falling off the test specimen, the pump is immediately stopped, and the height in the column is recorded in units of mm.

For each material, five tests should be repeated and the results should be averaged.

Acquisition Test

This test should be carried out at about 22+/−2° C. and at 35+/−15% relative humidity. The synthetic urine used in these test methods is commonly known as Jayco SynUrine and is available from Jayco Pharmaceuticals Company of Camp Hill, Pa. The formula for the synthetic urine is: 2.0 g/l of KCI; 2.0 g/l of $Na_2SO_4$; 0.85 g/l of $(NH_4)H_2PO_4$; 0.15 g/l $(NH_4)H_2PO_4$; 0.19 g/l of $CaCl_2$; ad 0.23 g/l of $MgCl_2$. All of the chemicals are of reagent grade. The pH of the synthetic Urine is in the range of 6.0 to 6.4.

Figure 2:
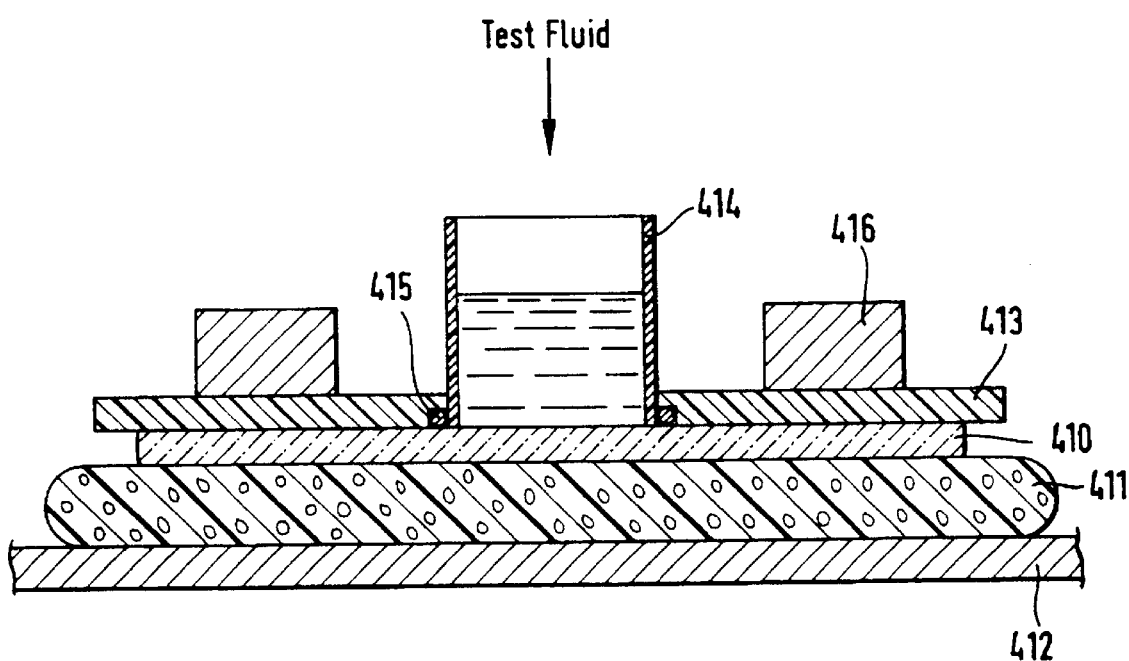
FIG. 2 is showing the test set up for the Acquisition Test.

Referring to FIG. 2, an absorbent structure (410) is loaded with a 75 ml gush of synthetic urine at a rate of 15 ml/s using a pump (Model 7520-00, supplied by Cole Parmer Instruments., Chicago, U.S.A.), from a height of 5 cm above the sample surface. The time to absorb the urine is recorded by a timer. The gush is repeated at precisely 5 minute gush intervals until the article is sufficiently loaded. Current test data are generated by loading four times.

The test sample, which can be a complete absorbent article or an absorbent structure comprising an absorbent core, a topsheet, and a backsheet, is arranged to lie flat on a foam platform 411 within a perspex box (only base 412 of which is shown). A perspex plate 413 having a 5 cm diameter opening in its middle is placed on top of the sample on the loading zone of the structure. Synthetic urine is introduced to the sample through a cylinder 414 fitted, and glued into the opening. Electrodes 415 are located on the lowest surface of the plate, in contact with the surface of the absorbent structure 410. The electrodes are connected to the timer. Loads 416 are placed on top of the plate to simulate, for example a baby's weight. A pressure of about 50 g cm-2 (0.7 psi) is achieved by positioning weights 416, e.g. for the commonly available MAXI size 20 kg.

As test fluid is introduced into the cylinder it typically builds up on top of the absorbent structure thereby completing an electrical circuit between the electrodes. The test fluid is transported from the pump to the test assembly by means of a tubing of about 8 mm diameter, which is kept filled with test fluid. Thus the fluid starts to leave the tubing essentially at the same time the pump starts operating. At this time, also the timer is started, and the timer is stopped when the absorbent structure has absorbed the gush of urine, and the electrical contact between the electrodes is broken.

The acquisition rate is defined as the gush volume absorbed (ml) per unit time(s). The acquisition rate is calculated for each gush introduced into the sample. Of particular interest in view of the current invention are the first and the last of the four gushes.

This test is primarily designed to evaluate products generally referred to as MAXI size products for a design capacity of about 300 ml, and having a respective Ultimate Storage Capacity of about 300 ml to 400 ml. If products with significantly different capacities should be evaluated (such as can be envisaged for adult incontinence products or for smaller babies), the settings in particular of the fluid volume per gush should be adjusted appropriately to about 20% of the total article design capacity, and the deviation from the standard test protocol should be recorded.

Figure 3:
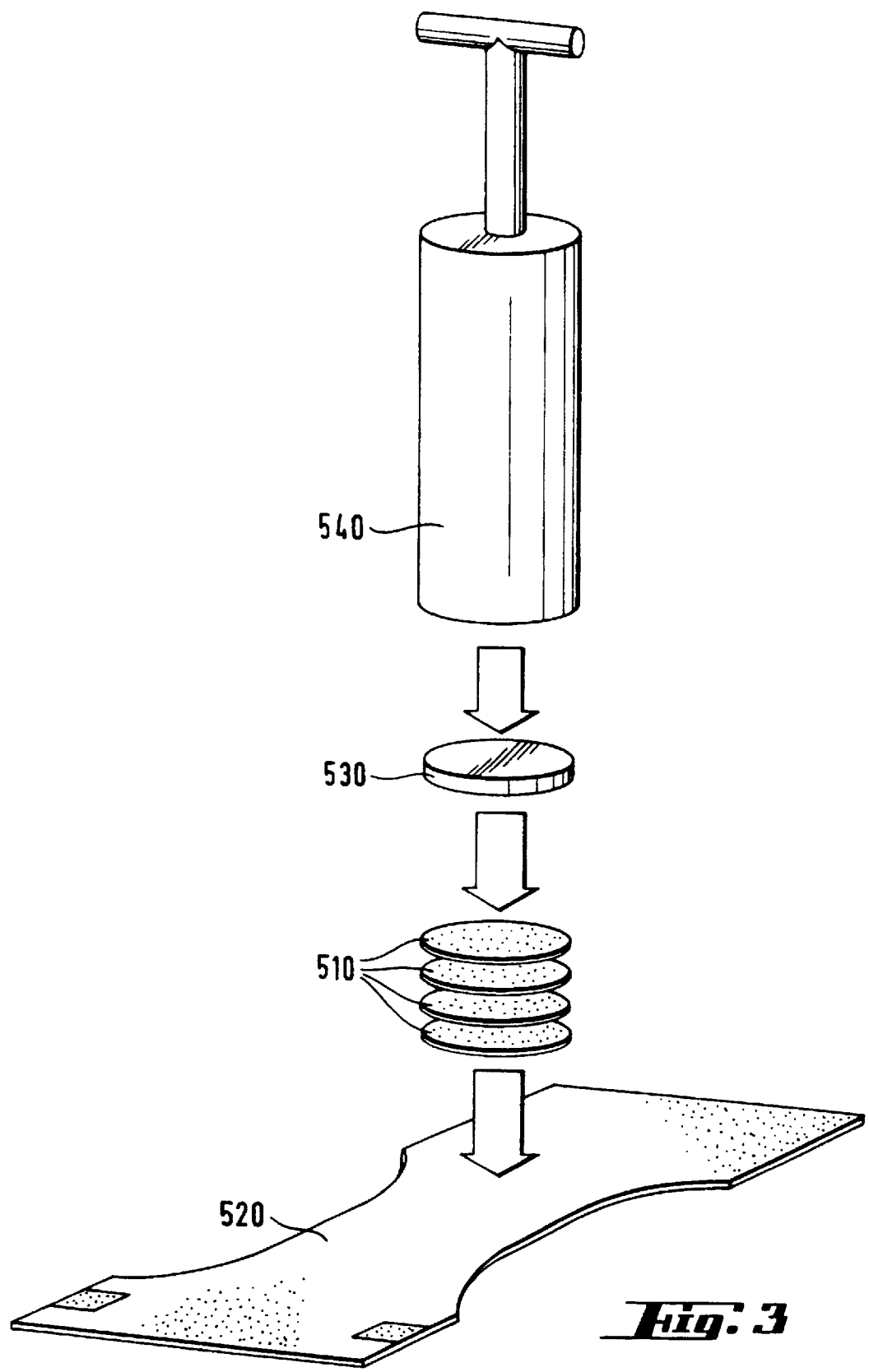
FIG. 3 is showing the test set up for the Post Acquisition Collagen Rewet Method.

Post Acquisition Collagen Rewet Method
(Refer to FIG. 3)

Before executing the test, the collagen film as purchased from NATURIN GmbH, Weinhein, Germany, under the designation of COFFI and at a basis weight of about 28 g/m$^2$ is prepared by being cut into sheets of 90 mm diameter e.g. by using a sample cutter device, and by equilibrating the film in the controlled environment of the test room (see above) for at least 12 hours (tweezers are to be used for all handling of the collagen film).

At least 5 minutes, but not more than 6 minutes after the last gush of the above acquisition test is absorbed, the cover plate and weights are removed, and the test sample (520) is carefully placed flat on a lab bench.

4 sheets of the precut and equilibrated collagen material (510) are weighed with at least one milligram accuracy, and then positioned centred onto the loading point of the article, and covered by perspex plate (530) of 90 mm diameter, and about 20 mm thickness. A weight (540) of 15 kg is carefully added (also centred). After 30+/-2 seconds the weight and perspex plate are carefully removed again, and the collagen films are reweighed.

The Post Acquisition Collagen Rewet Method result is the moisture pick up of the collagen film, expressed in mg.

It should be noted further, that this testing protocol can be adjusted easily according to specific product types, such as different baby diaper sizes, or adult incontinence articles, or catamenial articles, or by the variation in the type and amount of loading fluid, the amount and size of the absorbent material, or by variations in the applicable pressure. Having once defined these relevant parameters, such modifications will be obvious to one skilled in the art. When considering the results from the adjusted test protocol the products can easily be optimising these identified relevant parameter such as in a designed experiment according to standard statistical methods with realistic in use boundary conditions.

Teabag Centrifuge Capacity Test
(TCC Test)

Whilst the TCC test has been developed specifically for superabsorbent materials, it can readily be applied to other absorbent materials.

The Teabag Centrifuge Capacity test measures the Teabag Centrifuge Capacity values, which are a measure of the retention of liquids in the absorbent materials.

The absorbent material is placed within a "teabag", immersed in a 0.9% by weight sodium chloride solution for 20 minutes, and then centrifuged for 3 minutes. The ratio of the retained liquid weight to the initial weight of the dry material is the absorptive capacity of the absorbent material.

Two litres of 0.9% by weight sodium chloride in distilled water is poured into a tray having dimensions 24 cm×30 cm×5 cm. The liquid filling height should be about 3 cm.

The teabag pouch has dimensions 6.5 cm×6.5 cm and is available from Teekanne in Düsseldorf, Germany. The pouch is heat sealable with a standard kitchen plastic bag sealing device (e.g. VACUPACK2 PLUS from Krups, Germany).

The teabag is opened by carefully cutting it partially, and is then weighed. About 0.200 g of the sample of the absorbent material, accurately weighed to +/-0.005 g, is placed in the teabag. The teabag is then closed with a heat sealer. This is called the sample teabag. An empty teabag is sealed and used as a blank.

The sample teabag and the blank teabag are then laid on the surface of the saline solution, and submerged for about 5 seconds using a spatula to allow complete wetting (the teabags will float on the surface of the saline solution but are then completely wetted). The timer is started immediately. After 20 minutes soaking time the sample teabag and the blank teabag are removed from the saline solution, and placed in a Bauknecht WS130, Bosch 772 NZK096 or equivalent centrifuge (230 mm diameter), so that each bag sticks to the outer wall of the centrifuge basket. The centrifuge lid is closed, the centrifuge is started, and the speed increased quickly to 1,400 rpm. Once the centrifuge has been stabilised at 1,400 rpm the timer is started. After 3 minutes, the centrifuge is stopped.

The sample teabag and the blank teabag are removed and weighed separately.

The Teabag Centrifuge Capacity (TCC) for the sample of absorbent material is calculated as follows:

TCC=[(sample teabag weight after centrifuging)−(blank teabag weight after centrifuging)−(dry absorbent material weight)] ÷(dry absorbent material weight)].

Also, specific parts of the structures or the total absorbent articles can be measured, such as "sectional" cut outs, i.e. looking at parts of the structure or the total article, whereby the cutting is done across the full width of the article at determined points of the longitudinal axis of the article. In particular, the definition of the "crotch region" as described above allows to determine the "crotch region capacity". Other cut-outs can be used to determine a "basis capacity" (i.e. the amount of capacity contained in a unit area of the specific region of the article. Depending on the size of the unit area (preferably 2 cm by 2 cm) the defines show how much averaging is taking place—naturally, the smaller the size, the less averaging will occur.

What is claimed is:

1. A method for assessing at least one absorbent article, the method characterised in that it comprises the steps of
   (a) applying the absorbent article to a mannequin;
   (b) applying a relative humidity sensory probe between the article and the surface of the mannequin;
   (c) applying test fluid in one or more subsequent gushes with equilibration time therein between; and
   (d) monitoring a relative humidity reading.

2. A method according to claim 1, further characterised in that the end of the probe fits laterally centred about 5 cm backwards outwardly from a crotch point.

3. A method according to claim 1, further characterised in that when being applied for a MAXI size diaper, a gush volume in step (c) is 75 ml.

4. A method according to claim 1 wherein step (c) is repeated four times with 60 min waiting time, and the relative humidity reading is taken at least every 5 minutes.

5. A method according to claim 1 wherein the test fluid application rate is 150 ml/min.

6. A method according to claim 1 wherein the ambient testing conditions are set at 21±1° C. and 50±3% relative humidity.

7. A method according to claim 1, wherein the mannequin is in standing position.

* * * * *

UNITED STATES PATENT AND TRADEMARK OFFICE
CERTIFICATE OF CORRECTION

PATENT NO. : 6,446,495 B1  
DATED : September 10, 2002  
INVENTOR(S) : Herrlein et al.

It is certified that error appears in the above-identified patent and that said Letters Patent is hereby corrected as shown below:

Column 2,  
Line 60, after "the", delete ".".

Column 3,  
Line 38, delete "liners" and insert -- liner --.

Signed and Sealed this

Eighth Day of June, 2004

JON W. DUDAS  
*Acting Director of the United States Patent and Trademark Office*